(12) United States Patent
Kolovich et al.

(10) Patent No.: US 12,226,137 B2
(45) Date of Patent: Feb. 18, 2025

(54) ORTHOPEDIC IMPLANTS AND TOOLS

(71) Applicants: Gregory Paul Kolovich, Savannah, GA (US); Arden Joseph Hadwin, Jr., Savannah, GA (US)

(72) Inventors: Gregory Paul Kolovich, Savannah, GA (US); Arden Joseph Hadwin, Jr., Savannah, GA (US)

(73) Assignee: OC Medical Devices, LLC, Savannah, GA (US)

( * ) Notice: Subject to any disclaimer, the term of this patent is extended or adjusted under 35 U.S.C. 154(b) by 74 days.

(21) Appl. No.: 18/308,972

(22) Filed: Apr. 28, 2023

(65) Prior Publication Data

US 2024/0341826 A1 Oct. 17, 2024

Related U.S. Application Data

(63) Continuation of application No. 18/299,316, filed on Apr. 12, 2023, now Pat. No. 11,832,864.

(51) Int. Cl.
| | | |
|---|---|---|
| *A61B 17/88* | (2006.01) | |
| *A61B 17/72* | (2006.01) | |
| *A61B 17/86* | (2006.01) | |
| *A61F 2/46* | (2006.01) | |
| *A61B 17/00* | (2006.01) | |
| *A61B 90/00* | (2016.01) | |

(52) U.S. Cl.
CPC ...... *A61B 17/8875* (2013.01); *A61B 17/7283* (2013.01); *A61B 17/7291* (2013.01); *A61B 17/863* (2013.01); *A61B 17/8861* (2013.01); *A61F 2/4657* (2013.01); *A61B 2017/0092* (2013.01); *A61B 2090/0811* (2016.02); *A61B 2090/3966* (2016.02)

(58) Field of Classification Search
CPC ................................................. A61B 17/8875
See application file for complete search history.

(56) References Cited

U.S. PATENT DOCUMENTS

| | | | |
|---|---|---|---|
| 4,950,270 | A | 8/1990 | Bowman et al. |
| 5,019,080 | A | 5/1991 | Hemer |
| 5,403,136 | A | 4/1995 | Mathys |
| 5,743,914 | A | 4/1998 | Skiba |
| 5,871,486 | A | 2/1999 | Huebner et al. |
| 6,001,101 | A | 12/1999 | Augagneur et al. |
| 6,001,102 | A | 12/1999 | Barbera Alacreu et al. |
| 6,030,162 | A | 2/2000 | Huebner |
| 6,827,722 | B1 * | 12/2004 | Schoenefeld ...... A61B 17/1622 606/88 |
| 7,037,309 | B2 | 5/2006 | Weil et al. |
| 7,235,079 | B2 | 6/2007 | Jensen et al. |
| 7,537,596 | B2 | 5/2009 | Jensen |
| 7,731,738 | B2 | 6/2010 | Jackson et al. |

(Continued)

FOREIGN PATENT DOCUMENTS

WO  WO 2024/215510  10/2024

*Primary Examiner* — Christian A Sevilla
(74) *Attorney, Agent, or Firm* — Levine Bagade Han LLP

(57) ABSTRACT

Orthopedic implants for fixation of bone fractures to provide increase purchase of the orthopedic implant within specific regions of the repaired bone. Orthopedic accessory tools such as drill bits and multi-functional orthopedic sizing tools. Kits containing such orthopedic devices and methods for the use of such orthopedic implants, drill bits, and orthopedic tools.

6 Claims, 11 Drawing Sheets

(56) References Cited

U.S. PATENT DOCUMENTS

| | | |
|---|---|---|
| 8,128,671 B2 | 3/2012 | Taylor |
| 9,011,505 B2 | 4/2015 | Prandi et al. |
| 9,113,976 B2 | 8/2015 | Yevmenenko et al. |
| 9,131,946 B2 | 9/2015 | Larche et al. |
| 9,427,242 B2 | 8/2016 | Kam |
| 9,492,200 B2 * | 11/2016 | Sikora .................. A61B 17/683 |
| 9,498,262 B2 * | 11/2016 | Bankoski ............ A61B 17/7082 |
| 9,526,553 B2 * | 12/2016 | Bess ................... A61B 17/8875 |
| 9,585,703 B2 | 3/2017 | Munday et al. |
| 9,855,087 B2 * | 1/2018 | Divincenzo ........ A61B 17/7082 |
| 9,993,275 B2 | 6/2018 | Mildner et al. |
| 10,098,680 B2 | 10/2018 | Champagne et al. |
| 10,251,656 B2 | 4/2019 | Granberry et al. |
| 10,292,746 B2 | 5/2019 | Coillard-Lavirotte et al. |
| 10,531,905 B2 | 1/2020 | Gault et al. |
| 11,000,325 B2 | 5/2021 | Sommers et al. |
| 11,147,604 B2 | 10/2021 | Champagne et al. |
| 11,564,720 B2 | 1/2023 | Conley |
| 11,832,864 B1 | 12/2023 | Kolovich et al. |
| 12,035,951 B1 | 7/2024 | Kolovich et al. |
| 2001/0053935 A1 | 12/2001 | Hartdegen et al. |
| 2004/0068261 A1 | 4/2004 | Fourcault et al. |
| 2004/0082956 A1 | 4/2004 | Baldwin et al. |
| 2007/0233122 A1 | 10/2007 | Denis et al. |
| 2008/0041196 A1 | 2/2008 | Companioni et al. |
| 2008/0243136 A1 | 10/2008 | Prager et al. |
| 2010/0211118 A1 | 8/2010 | Christen et al. |
| 2014/0094859 A1 | 4/2014 | Reed |
| 2015/0265328 A1 | 9/2015 | Viola |
| 2016/0278789 A1 | 9/2016 | Garvey et al. |
| 2017/0135730 A1 | 5/2017 | Sauvage et al. |
| 2019/0262047 A1 | 8/2019 | Sommers et al. |
| 2021/0282828 A1 | 9/2021 | Champagne et al. |
| 2022/0054175 A1 | 2/2022 | Champagne et al. |
| 2022/0168034 A1 | 6/2022 | Lee et al. |

* cited by examiner

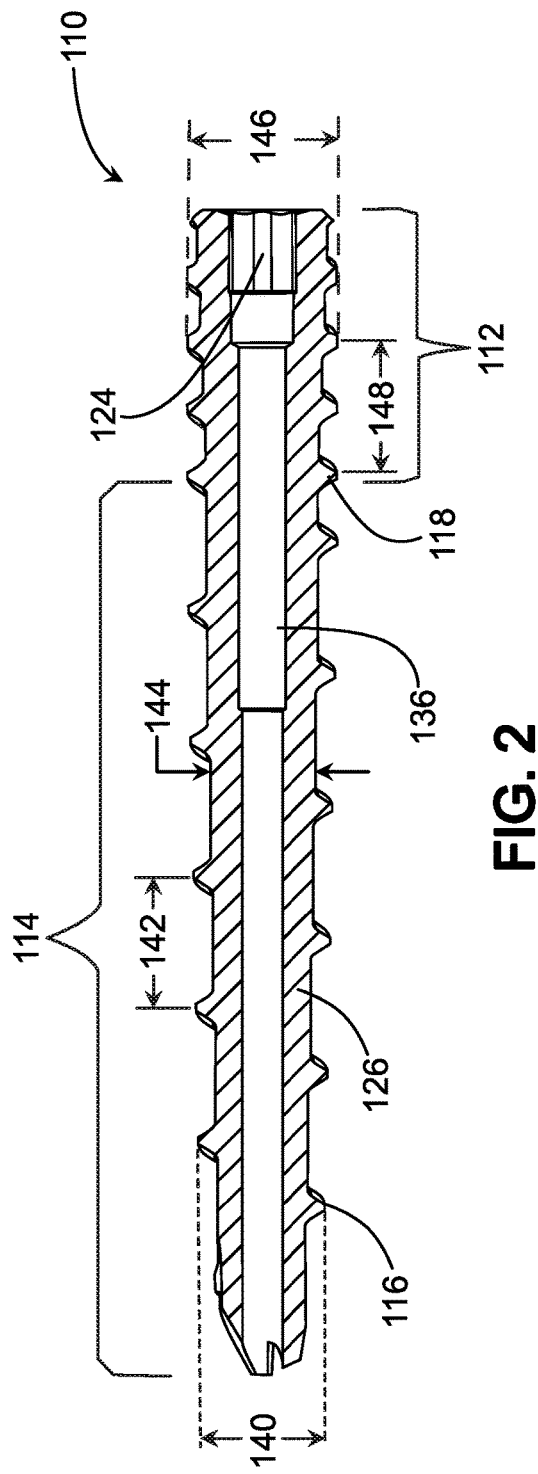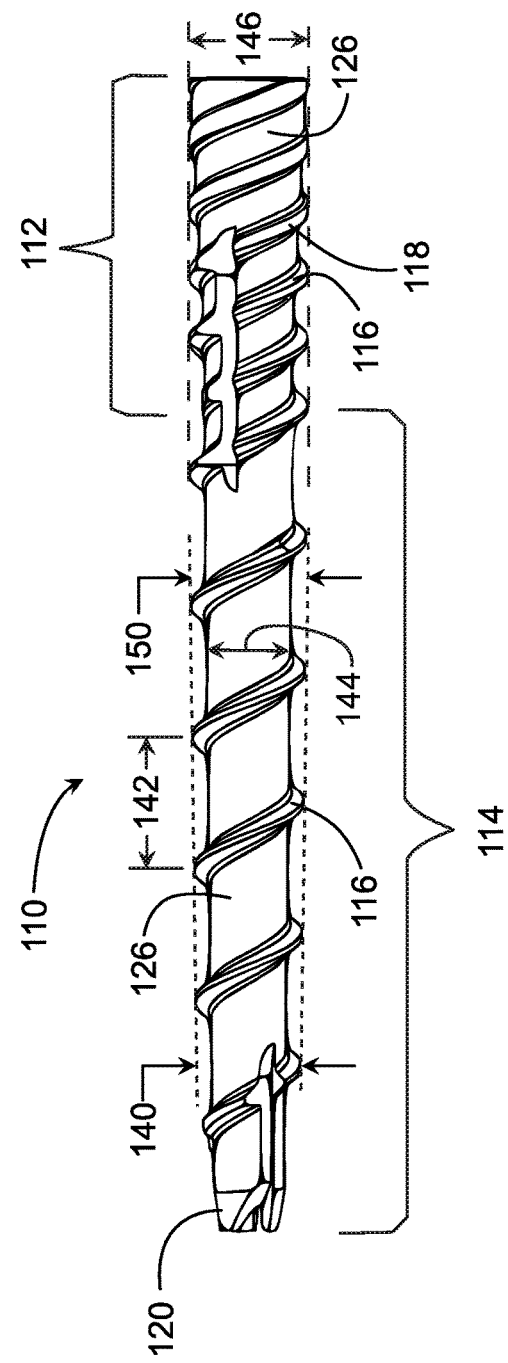
FIG. 2
FIG. 3A

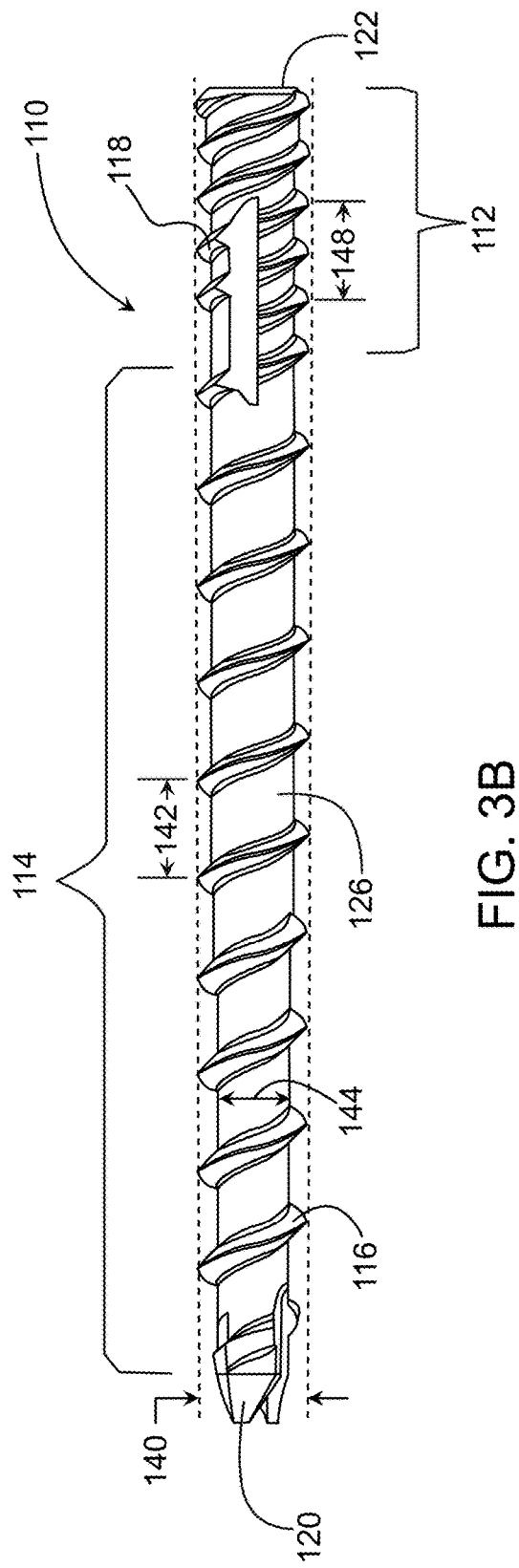
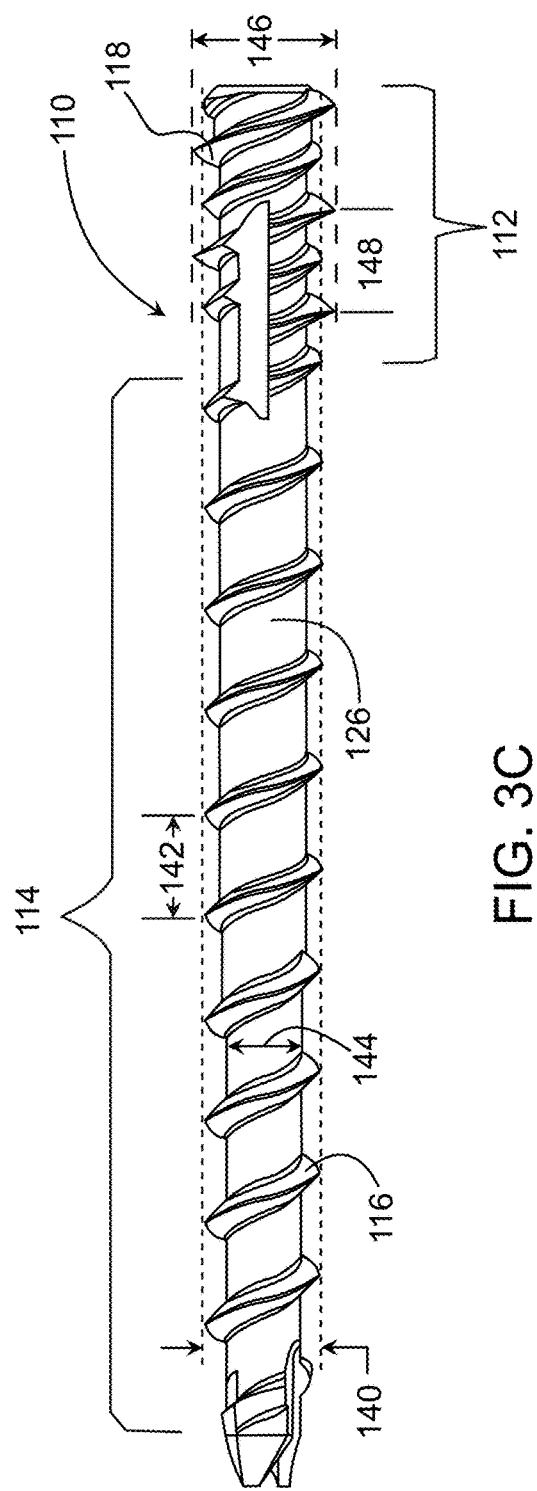
FIG. 3B
FIG. 3C

ORTHOPEDIC IMPLANTS AND TOOLS

CROSS-REFERENCE TO RELATED APPLICATIONS

This application is a divisional of U.S. patent application Ser. No. 18/308,972 filed Apr. 28, 2023, which is a continuation of U.S. patent application Ser. No. 18/299,316 filed Apr. 12, 2023, now U.S. Pat. No. 11,832,864, the entirety of each of which is incorporated herein.

FIELD OF THE INVENTION

The present disclosure relates to orthopedic implants for the fixation of bone fractures to provide increased purchase of the orthopedic implant within specific regions of the repaired bone. The present disclosure also relates to orthopedic accessory tools such as drill bits and multi-functional orthopedic sizing tools. The disclosure also includes various methods of use for such orthopedic implants, drill bits, and orthopedic tools, as well as kits containing such orthopedic devices.

BACKGROUND OF THE INVENTION

Implantable screw implants used to fixate broken bones have long been used in orthopedic surgery. More recent screw implant design includes (1) variable screw pitch, (2) screw cannulation, and (3) removing the screw head (headless screws). Variable screw pitch is a design by which the pitch decreases between the leading and trailing ends, thus causing reduction and compression across the fracture site as bone fragments are drawn together during screw installation.

Subsequent generations of orthopedic screw implants use the tenants described above in subsequent designs. In one case, a cannulated, headless screw was designed for the purpose of fixing metacarpal and metatarsal fractures in the hand and foot through an intramedullary approach. This screw design provided substantial circumferential cortical stability within the bone to strengthen its fixation and did not apply a compressive and therefore displacing force across the fracture upon intramedullary insertion. However, such screw designs had limited cortical fixation within the metacarpal and metatarsal neck. Examples of such screw implants can be found in the following patents and publications: U.S. Pat. No. 11,147,604 Bone Stabilization Device; U.S. Pat. No. 9,113,976 Headless Compression Screw with Integrated Reduction-Compression Instrument; U.S. Pat. No. 7,731,738 Cannulated Screw; U.S. Pat. No. 5,871,486 Variable Pitch Bone Screw; U.S. Pat. No. 11,564,720 Intramedullary Stabilization Screw; and US20220054175 Intramedullary Threaded Nail For Radial Cortical Fixation. The entirety of each of which is incorporated by reference.

In addition, there is a lack of an effective measuring tool to determine desired screw length and/or diameters. Typically, a surgeon can properly estimate the desired screw implant size and diameter by external assessment of the anatomy. However, in those cases of less experienced surgeons, the process of sizing a screw implant can increase the duration of the procedure. In those cases where an implanted screw is not properly sized, the implant must be removed from the anatomy, which causes additional trauma to the bone and surrounding anatomy, increases procedure time, and increases cost since the incorrectly sized screw is often discarded. Accordingly, there remains a need for an improved orthopedic tool that assists medical caregivers in implant selection as well as improving the efficiency of the procedure.

SUMMARY OF THE INVENTION

The devices of the present disclosure include orthopedic stabilization tools, implants, and kits, as well as methods of using one or more of such components.

In one variation, the present disclosure includes an orthopedic stabilization implant for use with an orthopedic tool and for implanting in a region of tissue having varying cross-sectional areas. For example, such an orthopedic stabilization implant can include an implant shaft having a distal region and a proximal region, the distal region terminating at a distal tip and the proximal region terminating at a proximal end; a first thread structure having a first major diameter and a first pitch, the first thread structure extending helically starting adjacent to the distal tip, over the distal region and over the proximal region, where the first pitch is consistent over the distal region and the proximal region; a second thread structure having a second major diameter and a second pitch, the second thread structure extending helically only along the proximal region, where the second thread structure is spaced from the first thread structure along the proximal region; a cannulated passage extending fully through the implant shaft; and a drive recess within the proximal end configured to receiving a drive structure of the orthopedic tool.

The orthopedic stabilization implant described herein can include varying structural details including a first major diameter that is constant in the proximal region, a first major diameter that is constant in the distal region, a first major diameter that increases in a distal-to-proximal direction in the distal region, a first major diameter that is constant, in the proximal region, a second major diameter that is constant. The second major diameter can be greater than the first major diameter or equal to the first major diameter in any region of the implant. Additional variations of the implant can include any variation described herein. The In an additional variation an orthopedic stabilization implant can include, wherein a diameter of the implant shaft that increases in the distal region in a distal-to-proximal direction. In additional variations, where the second major diameter is greater than the first major diameter in the proximal region.

In some variations, an orthopedic stabilization implant can be configured such that the second thread structure is 180 degrees out of phase with the first thread structure.

The implants described herein can include any number of self-tapping recesses, including one or more interruptions in the thread structures.

The present disclosure also includes an orthopedic tool for use with an orthopedic wire and an orthopedic implant selected from a plurality of orthopedic implants that vary in diameter and/or length, the surgical tool comprising. Such an orthopedic tool can include a second implant sizing surface located on the exterior of the shaft, where an outer dimension of the second implant sizing surface is greater than the outer dimension of the first implant sizing surface and corresponds to the desired diameter of the orthopedic implant.

The first implant sizing surface can be adjacent to the second implant sizing surface or can be spaced apart. Additionally, variations of the surgical tool can include a handle passage that opens at a surface of the handle to form a channel in the handle and where the plurality of length markers are adjacent to the channel.

The handle can also include a transparent portion adjacent to both the handle passage and to the plurality of length markers, such that proximal end of the orthopedic wire located in the handle passage is visible from an exterior of the handle through the transparent portion.

In some variations, the surgical tool has a handle where a portion or all of the handle is radio-translucent, and the shaft is radiopaque.

The surgical tool can also optionally include a drive surface that is located at the distal end of the shaft, where the drive surface is accepted by a drive recess of the orthopedic implant.

Variations of the present invention also include a surgical tool for use with an orthopedic wire and an orthopedic implant selected from a plurality of orthopedic implants varying in diameter and length, the surgical tool including: a driving shaft having a drive surface at a distal end and a shaft passage extending longitudinally through the drive surface and driving shaft, the drive surface configured to engage a drive recess of the orthopedic implant, at least one sizing surface on the driving shaft having a first sizing diameter greater than a driving shaft diameter, wherein the first sizing diameter corresponds to a desired diameter the orthopedic implant, wherein the driving shaft and the at least one sizing surface are radiopaque; and a handle located at a proximal end of the driving shaft, the handle further including a handle passage located therein adjacent to the shaft passage, a plurality of length markers identifiable from an exterior of the handle; wherein when a distal segment of the orthopedic wire is within the handle passage and extends out of the distal end through the shaft passage, a length marker from the plurality of length markers that is adjacent to a proximal end of the orthopedic wire permits identification of a desired length of the orthopedic implant.

The surgical tool can further include a second implant sizing surface located on the exterior of the driving shaft, where an outer dimension of the second implant sizing surface is greater than the outer dimension of the first implant sizing surface and corresponds to the desired diameter of the orthopedic implant.

The invention also includes methods for sizing an orthopedic implant intended for positioning in a cavity of an anatomic structure where an orthopedic wire extends from the cavity. In such a case, the method can include: advancing an orthopedic tool over a proximal portion of the orthopedic wire where the distal portion of the orthopedic wire is in the cavity, the orthopedic tool having a handle with a plurality of length markers visible from an exterior of the orthopedic tool; positioning a tip of the orthopedic tool adjacent to the anatomic structure where the proximal portion of the orthopedic wire remains within the orthopedic tool; determining a desired length of the orthopedic implant by identifying a length marker from the plurality of length markers that is adjacent to a proximal end of the orthopedic wire; and selecting a length of the orthopedic implant using the desired length.

A variation of the method includes an orthopedic tool that includes a shaft extending from the handle, with a tool passage extending through both the handle and the shaft, where positioning the tip of the orthopedic tool adjacent to the anatomic structure comprises positioning a distal end of the shaft at least adjacent to the anatomic structure and positioning the proximal portion of the orthopedic wire within the orthopedic tool. The method can also include selecting a length of an orthopedic drill bit from a plurality of orthopedic drill bits using the desired length.

In another variation, the present disclosure includes a method for sizing an orthopedic implant for positioning in a cavity of an anatomic structure having an orthopedic wire extending from the cavity. For example, a variation of the method includes: positioning an orthopedic tool over an exterior of the anatomic structure, where the orthopedic tool includes a driving shaft extending from a handle, a first implant sizing surface on the driving shaft and a plurality of length markers visible from an exterior of the handle; aligning the first implant sizing surface along an axial centerline of the anatomic structure; obtaining a non-invasive image of the first implant sizing surface and the anatomic structure; selecting a diameter of the orthopedic implant using the non-invasive image to compare an outer dimension of the first implant sizing structure to a diametric dimension of the cavity; feeding a proximal portion of the orthopedic wire within orthopedic tool; positioning a tip of the driving shaft adjacent to the anatomic structure where the proximal portion of the orthopedic wire remains within the orthopedic tool and a distal portion of the orthopedic wire remains within the cavity; determining a desired length of the orthopedic implant by identifying a length marker from the plurality of length markers that is adjacent to a proximal end of the orthopedic wire; and selecting a length of the orthopedic implant using the desired length; removing the orthopedic tool from the orthopedic wire; advancing the orthopedic implant having the diameter and the length into over the wire; and driving the orthopedic implant into the cavity using the orthopedic tool. Broad claim The methods described herein can also include methods of positioning an orthopedic implant in a cavity of an anatomic structure having an orthopedic wire extending from the cavity, the method including: providing an orthopedic tool adjacent to the anatomic structure, the orthopedic tool having one or more length markers; selecting a desired diameter by non-invasively imaging the orthopedic tool and the anatomic structure to non-invasively compare at least one sizing surface on the orthopedic tool to a diametric dimension of the cavity; placing the orthopedic wire into the orthopedic tool while a distal portion of the orthopedic wire remains in the cavity; positioning a distal tip of the orthopedic tool adjacent to the anatomic structure; determining a length marker from the one or more length markers that is adjacent to a proximal end of the orthopedic wire and using the length marker to select a desired length; selecting the orthopedic implant from a plurality of orthopedic implants, where the orthopedic implant includes the desired length and the desired diameter; removing the orthopedic tool from the orthopedic wire; advancing the orthopedic implant over the orthopedic wire; and driving the orthopedic implant into the cavity using the orthopedic tool.

In an additional variation, the methods can include for preparing for an orthopedic procedure in a cavity of an anatomic structure having an orthopedic wire extending from the cavity, the method including: positioning an orthopedic tool relative to a proximal portion of the orthopedic wire where the distal portion of the orthopedic wire remains in the cavity, matching a proximal end of the orthopedic wire to a marker on the orthopedic tool to determine a desired length; positioning the orthopedic tool adjacent to the anatomic structure and obtaining a non-invasive image to match a sizing surface on the orthopedic tool to an outline of the cavity, where the sizing surface corresponds to a desired diameter; and selecting an orthopedic implant from a plurality of orthopedic implants, where the orthopedic implant includes the desired length and the desired diameter.

Another variation includes a method where the orthopedic tool further includes a drive surface that nests within a drive recess of the orthopedic implant.

The method, devices, and kits of the present disclosure allow for a considerable number of combinations and permutations of different variations of the disclosed devices as well as combination of aspects of those structures and methods as well. It is contemplated that any of the elements described with respect to any variation can be combined with any other variation.

BRIEF DESCRIPTION OF THE FIGURES

FIG. 2 shows a cross-sectional side view of the implant of FIG. 1.

FIGS. 3A to 3C illustrates variations of orthopedic implants.

DETAILED DESCRIPTION

Although the following disclosure includes specific variations and examples of orthopedic implants, those of skill in the art will appreciate the disclosure extends beyond the specifically disclosed embodiments and/or uses and obvious modifications and equivalents thereof. For example, variations of the methods, systems, and devices, which include implants, drill bits, and orthopedic tools, as described herein, are discussed for use in intramedullary fixation. However, the methods, systems, and devices described herein can also be used in other orthopedic procedures in various bone structures or in various other parts of a body. The discussion of intramedullary fixation is intended to provide one example to illustrate the various features and aspects of the inventions as described herein. The scope of this disclosure can apply to multiple areas, not just limited to intramedullary fixation.

In one general aspect, variations of orthopedic stabilization implants described herein can have selected aspects and features that improve upon prior existing technology in a number of ways. In many cases, a metacarpal fracture involves a fracture pattern in the bone that is prone to deformation of the associated body structure due to the compressive forces applied on the bone by adjacent muscles (e.g., interosseous muscles). Therefore, in most procedures, the physician must place the body structure in tension to reduce the fracture/deformation. The design of the implants themselves can provide substantial circumferential cortical stability within a damaged bone to strengthen the bone after fixation. Therefore, a portion of the implant can have a shaft and first thread structure that does not apply a significant compressive force that would otherwise displace the damaged bone structure upon intramedullary insertion of the implant. This also prevents the insertion of the implant from working against the physician during reduction of the fracture (i.e., the physician applies tension to the bone structure, while the insertion of the implant applies little or no compressive forces). In addition, implants of the present disclosure can comprise one or more segments on the implant that result in expanding the purchase or grip of the implant within a metacarpal neck region, which has a greater volume than an intermediate portion of the metacarpal. For example, a proximal region(s) can be configured to increase the purchase of the implant, while the distal region(s) can be configured to reduce compressive force during insertion. Moreover, the implants of the present disclosure can be part of a system that is used with an orthopedic tool that also serves as a measuring device to improve measuring accuracy and procedural efficiency.

Figure 1:
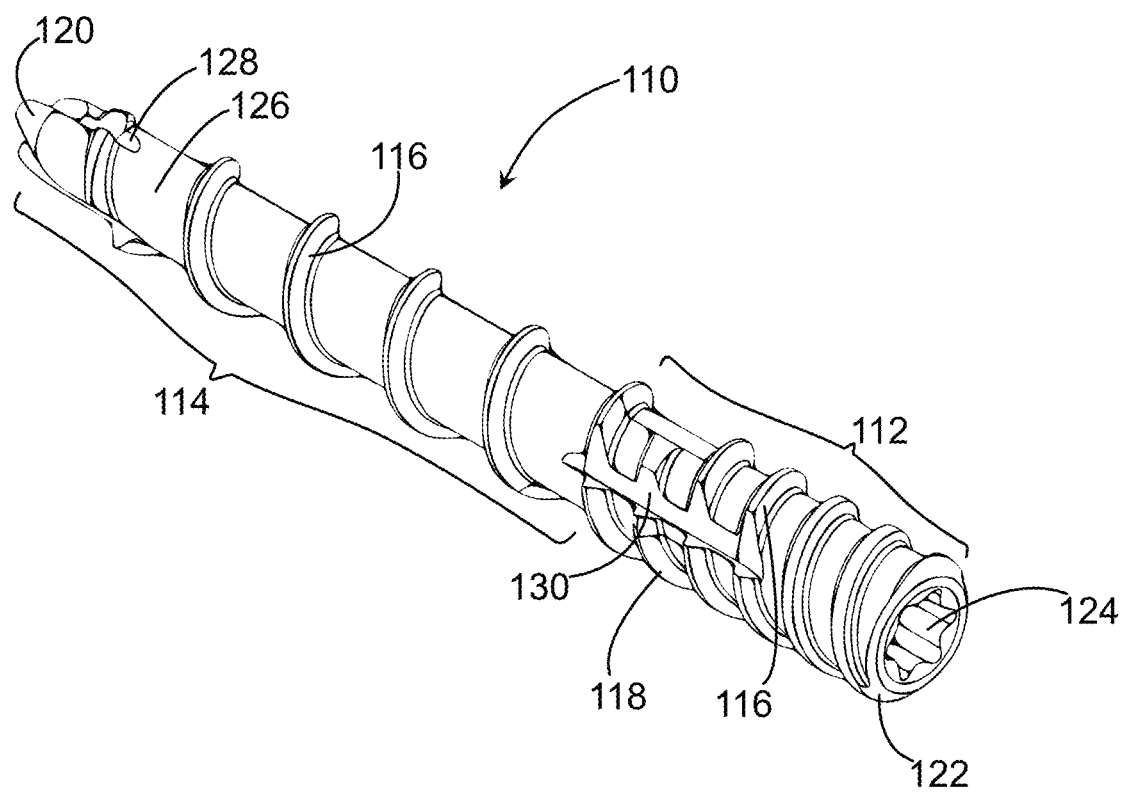
FIG. 1 shows an example of improved orthopedic implants for the stabilization of broken or fractured bones.

FIG. 1 shows an example of improved orthopedic implants for the stabilization of broken or fractured bones. As discussed herein, the configurations of implant 110 shown in FIG. 1 have features and aspects that result in varying properties across the lengths of the implant during the act of implantation and when implanted. As discussed below, any of the diameters, lengths, and pitches can be altered, increased, or otherwise adjusted for the desired purpose of the orthopedic implant. Therefore, any combination of features discussed below is within the scope of the invention for the purposes of any claim. The implant 110 shown in FIG. 1, as well as the implants discussed below, are provided for discussion of the various features and components of implants where different variations of any feature or component still remain within the scope of this disclosure.

As shown, implant 110 includes a first threaded structure 116 (first thread) that runs from a distal tip 120 of a shaft 126 to a proximal region 112 of the shaft 126. In some variations, the first thread 116 extends to a proximal end 122 of the shaft 126, either fully to a proximal end 122 or spaced from the proximal end 122. The implant 110 includes a second threaded structure 118 (second thread) limited to the proximal section 112 of the implant. The thread structures are configured to cut into bone upon rotation of the implant 110. The presence of both thread structures 116 118 in the proximal region 112 increases the purchase of the implant within a metacarpal head or neck. The proximal region 112 generally starts at a location on the shaft having properties that are different than the distal region. Variations of the devices include proximal and distal regions that are immediately adjacent, spaced apart, or overlap.

The distal end 120 of the shaft 126 is also configured to cut into bone or hard tissue. Moreover, variations of the implant 100 can include one or more periodic interruptions 126, 130 in one or both threads 116, 118 in the thread(s) to permit the threads to perform a self-tapping function upon insertion and rotation within hard tissue. Similarly, the thread structures 116 118 are configured with a narrowing crest such that they cut into bone structures. As shown and discussed below, the first and second threads 116, 118 on the proximal region 112 are spaced. In one variation, the start of the second thread 118 is 180 degrees out of phase or offset from the start of the first thread 116.

FIG. 1 shows the proximal end 122 of the implant 110 having a drive recess 124 that accommodates a mating orthopedic tool, as discussed below (not shown in FIG. 1).

Typically, such a recess can accommodate a Torx or hexalobular drive. However, variations of the implants described herein can include a recess that is configured to accommodate any number of different drive structures. The variation of implant 110 shown in FIG. 1 comprises a "headless" implant design, in which the drive recess 124 is within the interior of the screw shaft 126 such that one or more threads extend over an exterior of the shaft 126 adjacent to the recess 124. However, variations of implants under the present disclosure can include a drive recess 124 that is within a portion of the shaft that contains no threaded structure or even has a raised exterior surface that forms a head of the implant.

FIG. 2 shows a cross-sectional side view of implant 110 of FIG. 1. As shown, the first thread structure 116 extends over the distal segment 114 and the proximal segment 112 of the implant 110. The first thread structure 116 can include a major diameter 140. Typically, the major diameter is a diameter of an imaginary cylinder formed around the crest of an external thread. As shown, the major diameter 140 of the first thread structure 116 can be measured as the distance between the crest of the threads 116 on opposite sides of the shaft 126. However, as discussed below, variations of the implant 110 can include thread structures having major diameters that vary along the implant's 110 length. The first thread structure 116 also includes a first pitch 142, which is the distance between adjacent crests. As noted above, variations of the implant 110 include a first thread structure 116 having a constant first pitch 142, which minimizes compression forces during intramedullary insertion of the implant. The proximal region 112 of the implant 110 includes a second thread structure 118 having a second major diameter 146 and pitch 148 measured in a similar manner as the pitch and major diameter of the first thread structure 116. The implant 110 also includes a shaft 126 diameter 144, which can remain constant or vary over one or more regions of the implant 110. The implant 110 can also include a passage 136 that extends through the shaft 126 and is open at recess 124. Passage 136 accommodates advancing the implant 110 over an orthopedic wire or other guide, as discussed below. Alternate variations of the implant 110 do not require passage 136.

FIG. 3A illustrates one variation of an implant 10 where a first thread structure 116 comprises a major diameter 140 that increases along the distal segment 114 towards the proximal segment 112 (in a distal-to-proximal direction) to a major diameter 150. Variations of the device include the major diameter 150 adjacent to the proximal region 112 being equal to or greater than a major diameter 146 of the thread structure in the proximal region. Alternatively, the major diameter 150 in this region can remain less than the major diameter in the proximal region 112.

In the illustrated variation, the first thread structure 116 has a pitch 142 that remains constant over at least the distal region 114. Variations of implants can include a first thread structure 116 where the pitch 142 also remains constant over the proximal segment 118. Alternatively, variations of devices can include a first thread structure 116 where a pitch 142 increases or decreases in the proximal segment 112. Similarly, a diameter 144 of the shaft 126 can increase over the distal region 114 and can optionally continue to increase over the proximal region 112. In the variation shown in FIG. 3A, while the diameter 144 of the shaft 126 increases in the proximal region 112, the major diameters of the first and second thread structures can remain constant (as shown by 146).

FIG. 3B illustrates an additional variation of an implant 110 having a first thread structure 116 extending across the distal segment 114 and proximal segment 112 of the shaft 126 and a second thread structure 118 limited to the proximal segment 112. Both threads 116 118 comprise the same major diameters 140, and the pitch 142 of the first thread structure is the same as the pitch 148 of the second thread structure 118. Moreover, a diameter 144 of the shaft 126 increases in a distal-to-proximal direction (e.g., from the tip 120 to the proximal end 122 of the shaft.)

FIG. 3C illustrates another variation of an orthopedic stabilization implant 110 having a first thread structure 116 with a first major diameter 140 that remains constant across the distal segment 114 and proximal segment 112, but where the second thread structure 118 has a second major diameter 146 that is greater than the first major diameter 140.

The orthopedic stabilization implants can be manufactured from a variety of materials commonly used for orthopedic implants. In one example, such implants can be manufactured from an anodized titanium alloy for strength and biocompatibility. In addition, the implants can vary in length and diameter to accommodate the intended anatomy. Examples include implants in at least 2 diameters (3.6 mm and 4.5 mm) and lengths ranging from 25 mm to 75 mm.

Figure 4:
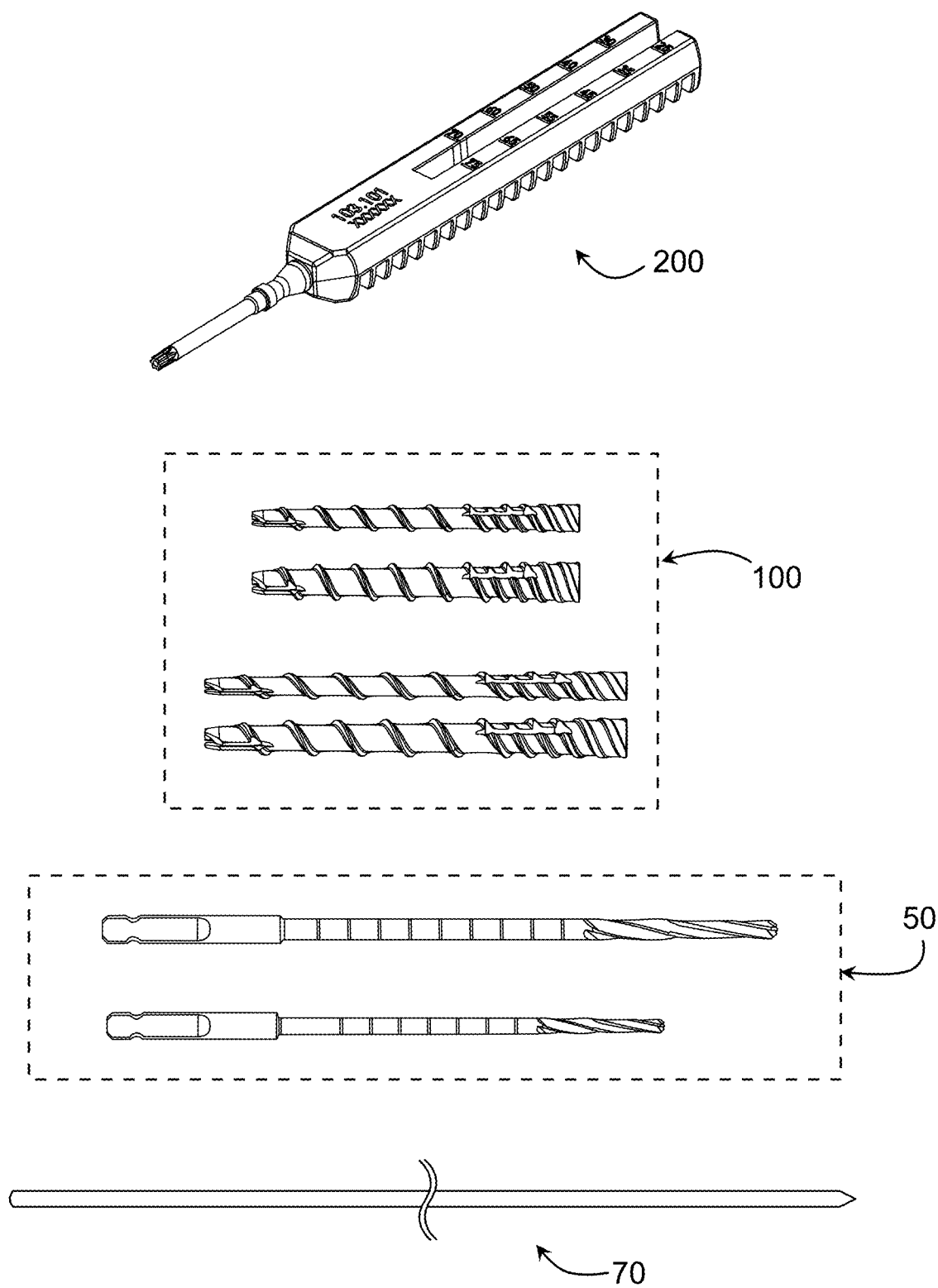
FIG. 4 illustrates an example of components for an orthopedic kit for use in orthopedic stabilization procedures.

FIG. 4 illustrates a sample kit for use in orthopedic stabilization procedures. As shown, the kit can include one or more components comprising: an orthopedic tool 200, a plurality of orthopedic stabilization implants 100, one or more drills 50, and one or more orthopedic wires. As illustrated, the implants 100 can comprise different diameters and lengths. Moreover, the implants can comprise multiple configurations as described herein or a number of implants that have the same features. Likewise, drills 50 can comprise different lengths and/or diameters. The kit can also include one or more orthopedic wires 70. For purposes of this disclosure and the claims, unless specifically indicated otherwise, the term orthopedic wire includes pins, cannulas, wires (such as a Kirschner wire), or other tubular/guiding structures that are used in orthopedic or other surgical procedures. Moreover, as described below, the orthopedic wires 70 can comprise selected axial lengths specifically designed for use with measuring features of the orthopedic tool.

Figure 5A:
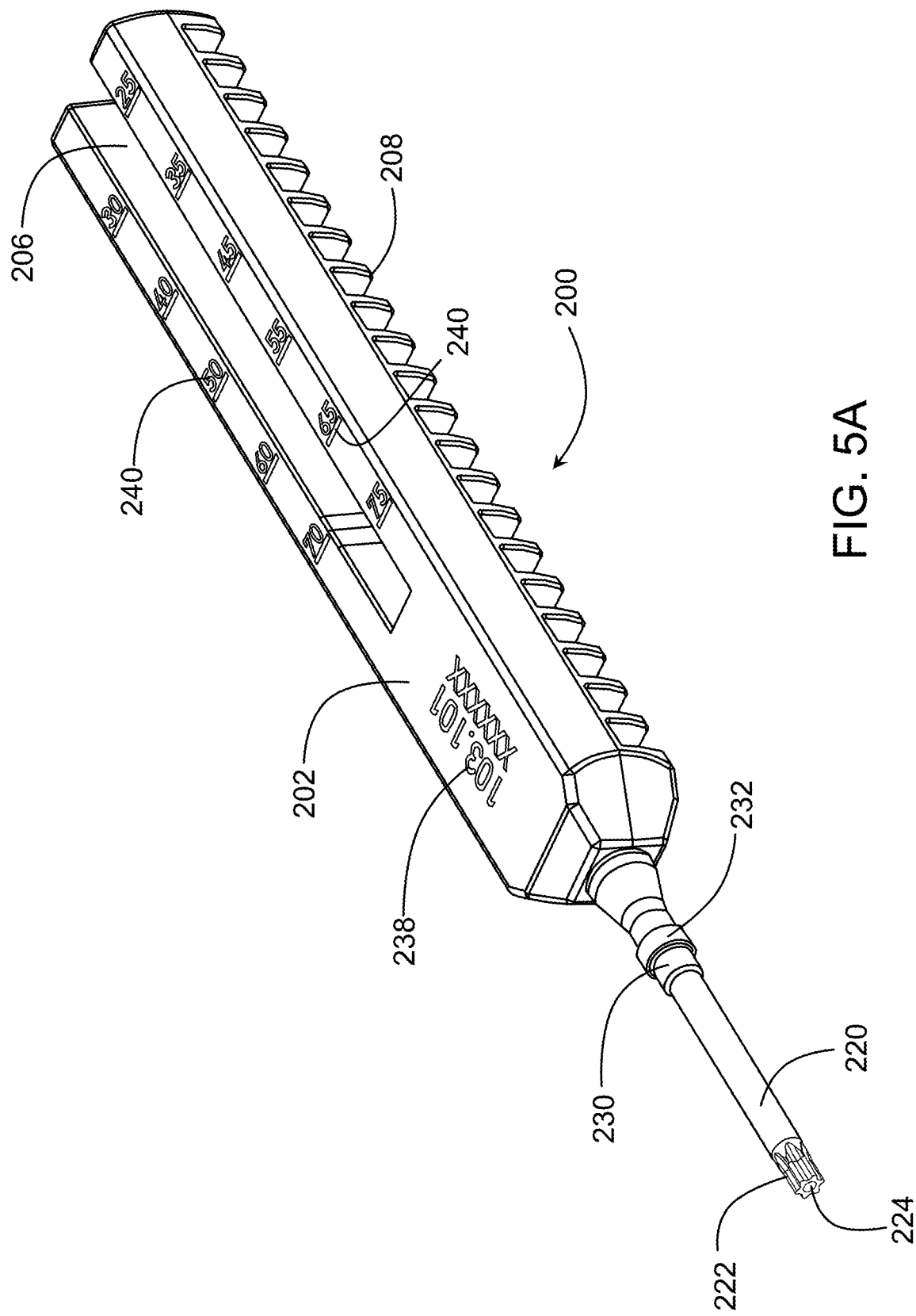
FIG. 5A illustrates one example of a combination orthopedic tool 200 that can be used for determining the length and diameter sizing of an implant prior to a procedure.

FIG. 5A illustrates one example of a combination orthopedic tool 200 (referred to as an orthopedic tool for convenience) that can be used for determining length and diameter sizing of an implant prior to a procedure. The orthopedic tool 200 improves the accuracy of implant selection and increases the efficiency of implant placement. In additional variations, the orthopedic tool 200 is also used for insertion of the orthopedic implant within the anatomic structure. As shown, the orthopedic tool 200 includes a body 202 having one or more recesses 206 that allow use of an orthopedic wire to determine length selection of an implant as discussed below. The recess 206 can be an open channel or cavity. Alternatively, the recess 206 can comprise an opening that is covered by a transparent/translucent covering, which can assist in preventing inadvertent contact with a proximal portion of the orthopedic wire during the measurement process. The body 202 of the orthopedic tool 200 can include any number of ergonomic or other features that assist the physician in manipulating the tool 200 during a procedure. For example, the handle 202 can include any number of surface features 208 that improve the ability of the user to grip the tool 200. In addition, the orthopedic tools 200 described herein are not limited for use with the orthopedic implants described herein. The orthopedic tools 200 can be used with any commercially available implant and/or orthopedic wire so long as the orthopedic wire has a length that permits accurate determination of a desired length of an orthopedic implant.

The body 202 of the orthopedic tool 200 includes a number of length markers 240 that are identifiable from an exterior of the device 200. In the illustrated variation shown in FIG. 5A, the markers 240 comprise numbering that is printed, etched, raised, or engraved on a surface of the body 202. However, in additional variations, the length markers 240 can be located within the recess 206 or on any other part of the device 200. Moreover, the length markers 240 can comprise numbers, letters, colors, symbols, tactile indicators, or a combination thereof that allow a caregiver to select a desirable length implant based on the measurement process discussed below.

The orthopedic tool 200 further includes a shaft 220 extending at a distal end. The shaft 220 in the illustrated variation comprises a cylindrical shape. However, other shapes are within the scope of this disclosure. In variations of the device, the shaft comprises a hardened material (e.g., stainless steel) that is radiopaque, while the handle body 202 comprises a radio-translucent material (e.g., a PEEK material). The shaft 220 can include a drive surface 222 that nests within an implant (as discussed above). The drive surface 222 can comprise a Torx or hexalobular drive surface. In those variations of the orthopedic tool 200 that include a drive surface 222, the combination tool 200 increases efficiency of the physician by use of the same tool for length and/or diametrical measurements for sizing the implant as well as driving of the implant into tissue. Alternatively, variations of the tool 200 can include just one or more of the measurement components. In addition, alternate variations of the device 200 can include a drive surface 222 having a standard screwdriver, rachet, or other drive surface to accommodate an associated implant. In the illustrated variation, the shaft 220 includes a passage 224, that extends through the shaft and into the recess 206. As will be discussed below, this permits passage of an orthopedic wire into the device 200 to determine a length of the intended implant.

FIG. 5A also shows the shaft 220 as including a number of sizing surfaces 230, 232. These sizing surfaces 230, 232 can be radiopaque and are sized to corresponding implants of varying diameters. While the variation shows two sizing surfaces 230, 232, alternate variations of the tool 200 can include a single sizing surface. In such a case, the diameter of the shaft 220 can serve as a first sizing surface and a second raised sizing surface on the shaft provides an increased diameter for matching with an implant of a corresponding diameter. The sizing surfaces can be cylindrical or have other non-cylindrical shapes. In addition, the sizing surface can comprise a radiopaque component within a radio-translucent outer body as long as the radiopaque component allows a caregiver to associate the component with a desired diameter of an implant. Additionally, the sizing surfaces 230, 232 can be positioned on other parts of the device 200 as long as the physician is able to compare the surfaces 230, 232 against anatomy during a non-invasive imaging procedure. For example, the shaft 220 will typically extend into the handle body 202 and the sizing surfaces can be positioned on the shaft 220 but within the body 202. Variations of the tool 200 include sizing surfaces that are permanently affixed to the shaft 220 or sizing surfaces that can be inserted onto the shaft prior to a procedure, which allows for a greater range of diametric sizes. For example, if a particular kit includes implants of four different diameters, a tool 200 can include four different sizing surfaces where one or more of the surfaces can be positioned onto the shaft as required by the anatomy.

Figure 5B:
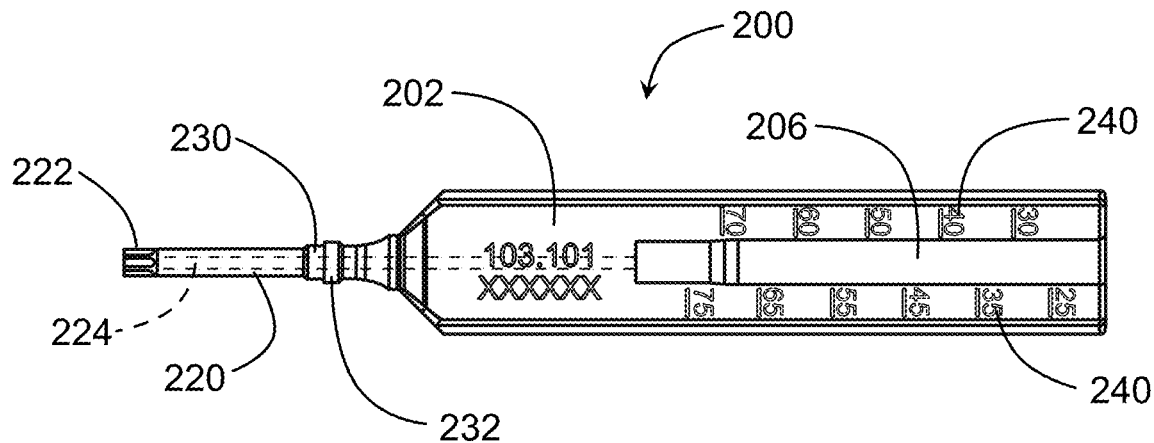
FIGS. 5B and 5C provide top views of alternate designs of orthopedic tools.
Figure 5C:
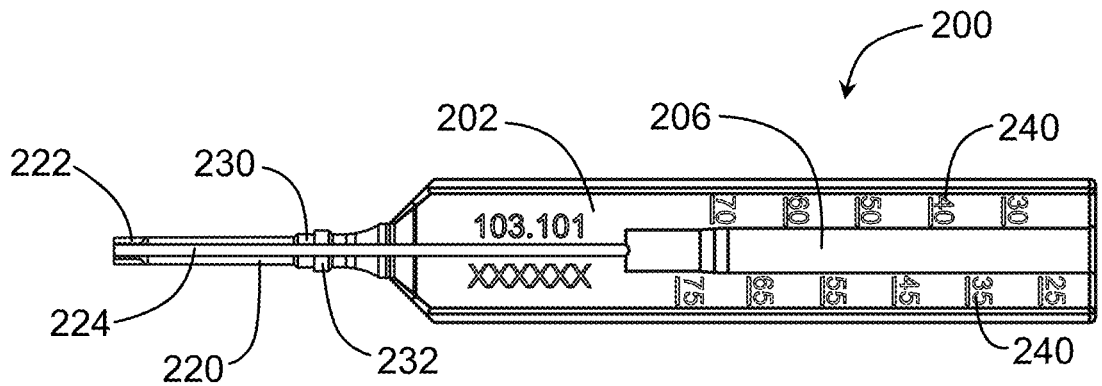
Figure 5D:
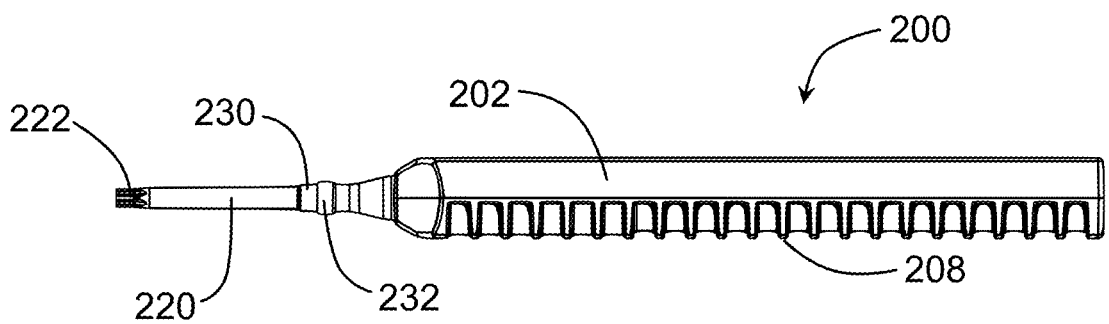
FIG. 5D shows a side view of a variation of an orthopedic tool.

FIGS. 5B and 5C provide top views of alternate designs of orthopedic tools 200. Where FIG. 5D shows a side view of the orthopedic tool 200. As shown, the orthopedic tool 200 of FIG. 5B includes a passage 224 that extends coaxially through a shaft 220 from the drive surface 222 to the channel 206 in the body 202 so that the device 220 can be advanced over an implanted orthopedic wire (not shown). Alternatively, FIG. 5C illustrates a passage 224, that is open along a surface of the shaft 220 and the body 202. This variation allows for non-axial insertion of an orthopedic wire into the device 200. In either case, the proximal end of the orthopedic wire extends within the body 202, where the length markers 240 permit selection of a length of the desired implant using a length of the orthopedic wire. The sizing surfaces 230, 232 are located on the shaft 220. Again, any variation of the device 200 can include one or more raised sizing surfaces on the shaft. In any variation of the device, the shaft can serve as a sizing surface along with an additional raised sizing surface (e.g., 230, 232). However, in such cases, the driving surface 222 will be undersized relative to diameter of the shaft 220.

FIGS. 6A to 6G provide illustrations to show an example of the use of an orthopedic tool 200 for sizing an implant, sizing a drill bit, and driving the implant into anatomy. As noted above, the illustrations focus on use of an implant and tool for positioning in a hand 2 of an individual. However, the implant, orthopedic tool, kits, systems, and methods described herein can be used in any part of the anatomy where features of the claimed devices can be beneficial.

Figure 6A:
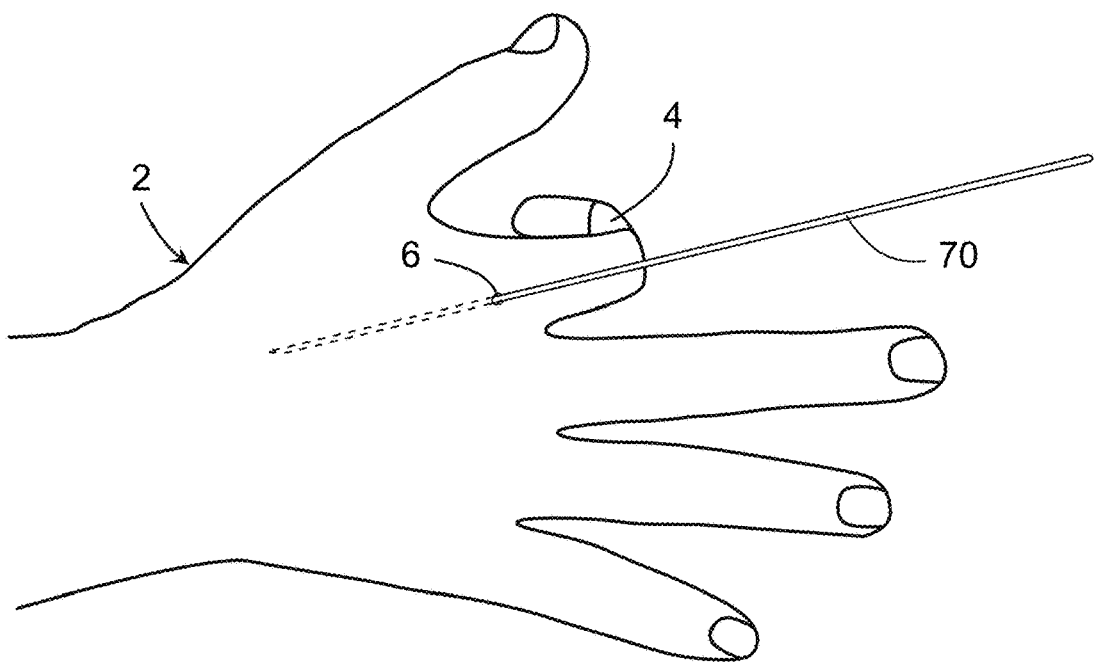
FIGS. 6A to 6G provide illustrations to show an example of the use of an orthopedic tool for sizing an implant, sizing a drill bit, and driving the implant into anatomy.

FIG. 6A illustrates a finger 4 of a hand 2, where the finger is curled in a downward direction to allow insertion of an orthopedic wire 70 within an opening 6 in the hand, where the orthopedic wire 70 is ultimately positioned within the anatomic structure. In this case, a metacarpal bone, using standard procedures. The act of placing the orthopedic wire 70 is a commonly known procedure. However, using an orthopedic tool, as discussed below, for determining the length of an implant requires use of an orthopedic wire 70 having a length that permits accurate measurement along the orthopedic tool. Therefore, orthopedic wires 70 used with the orthopedic tools described herein will have a length that is specific to the orthopedic tool.

Figure 6B:
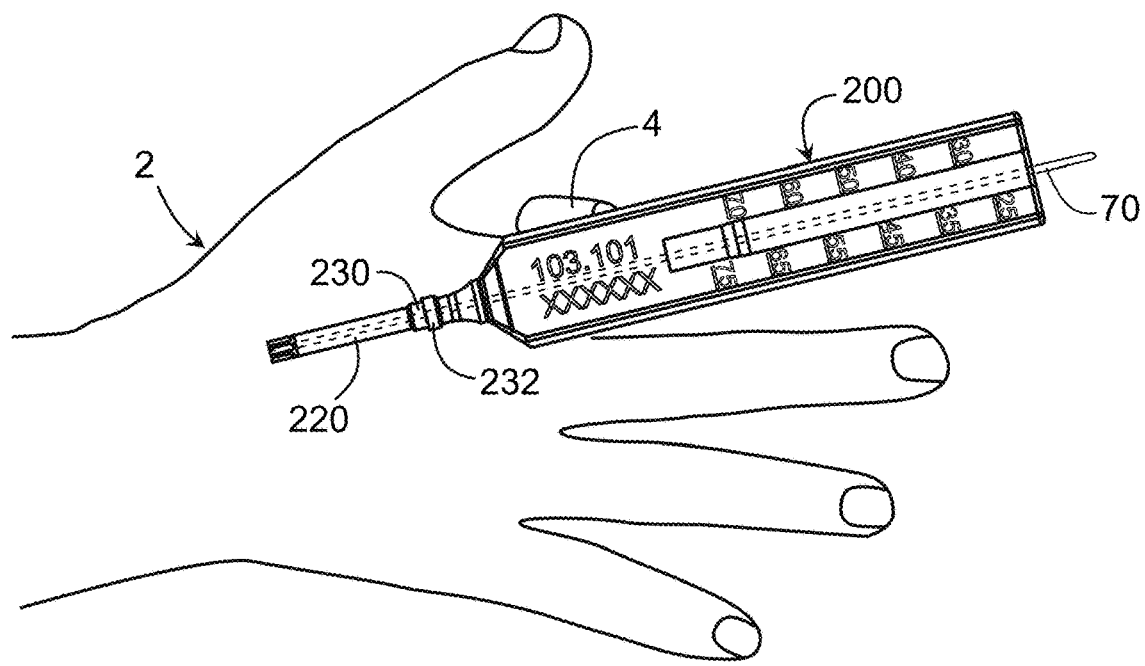

FIG. 6B is an illustration of an orthopedic tool 200 positioned on an exterior of an individual's hand 2 and adjacent to a target location, in this case a metacarpal bone. As shown, the orthopedic tool 200 is positioned over the orthopedic wire 70. In alternate variations, the orthopedic tool 200 can be positioned exterior to the anatomy before placement of the orthopedic wire 70. Typically, a caregiver will identify an end of the metacarpal bone and position the shaft 200 in alignment with the metacarpal bone such that sizing surfaces 230, 232 are aligned with the metacarpal bone. As noted herein, the illustrated device 200 shows two sizing surfaces, 230, 232, that are each associated with implants having respective diameters. The sizing surfaces 230, 232 can be undersized or oversized relative to the actual implant or can have the same respective diameters of their associated implant. Also, the orthopedic device 200 can have any number of sizing surfaces that allow selection of implants of varying diameters from a plurality of implants.

Figure 6C:
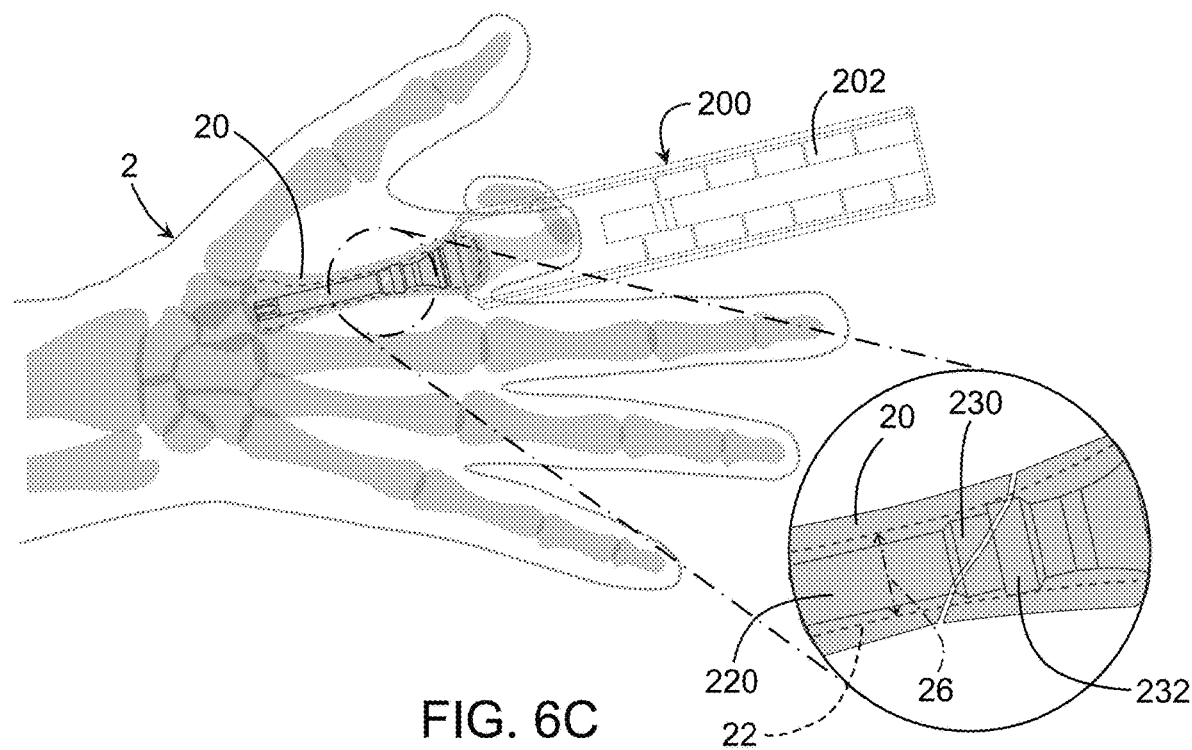

FIG. 6C represents a non-invasive image of the orthopedic tool 200 over the hand 200 with an expanded view of the shaft 220 and sizing surfaces 230, 232 over a cavity 22 of a metacarpal bone 20. The present illustration depicts an X-ray image where the shaft 220 is radiopaque while the body 202 of the orthopedic tool 200 is radiolucent such that it faintly shows on the X-ray image. It is contemplated that other non-invasive imaging modalities can be used while remaining with the scope of this disclosure. Using the non-invasive image, the caregiver is able to visually match one of the sizing surfaces 230, 232 with the diametric dimension 26 of the metacarpal cavity 22. In the illustrated variation (as shown in the expanded view), the first sizing feature 230 matches the diametric dimension 26 of the cavity 22. Accordingly, using this process, the caregiver can identify a desired diameter for the implant to be positioned in the metacarpal bone 20.

Figure 6D:
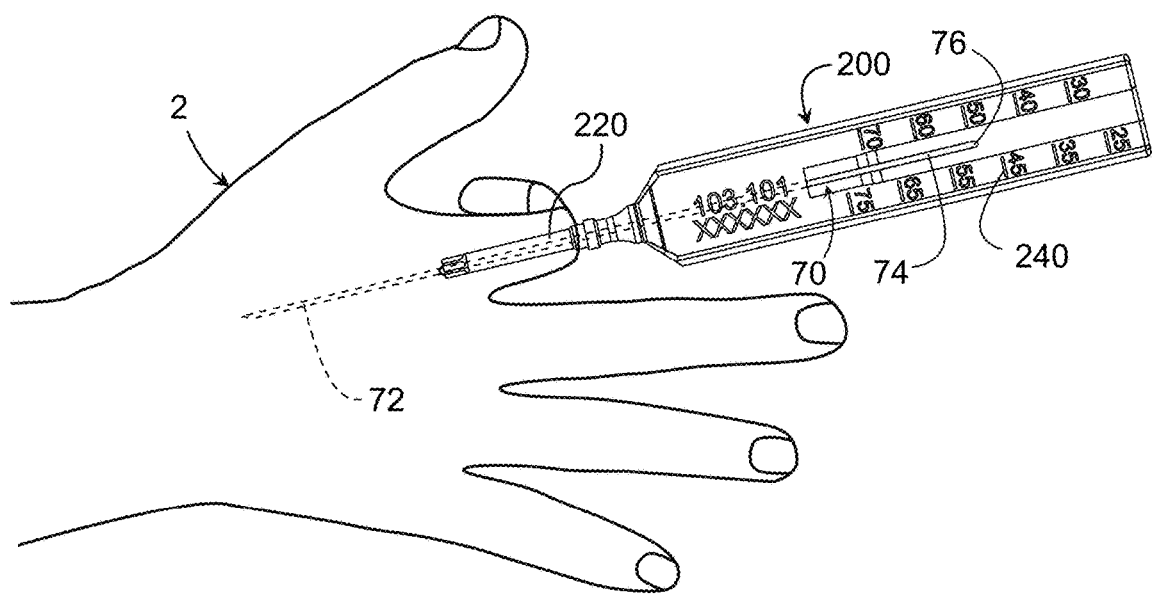

FIG. 6D illustrates an additional use of the orthopedic tool 200 to identify a desired length of an implant. It is noted that while the orthopedic tool 200 allows for both diameter and length sizing of an implant unless specifically recited, the methods disclosed do not require both diameter and length sizing. A caregiver may choose to use the orthopedic tool 200 for any one or a combination of diameter sizing, length sizing, and/or driving the implant into tissue. As shown in FIG. 6D, the caregiver positions the orthopedic wire 70 into the orthopedic tool 200, while a distal portion 72 of the wire 70 remains positioned in the anatomy 2, and a proximal portion 74 of the wire 70 is adjacent to length markers 240 of the orthopedic tool 200. Next, the caregiver can identify one or more length markers 240 that are adjacent to a proximal end 76 of the orthopedic wire 70 for identification of a desired length of the implant.

Figure 6E:
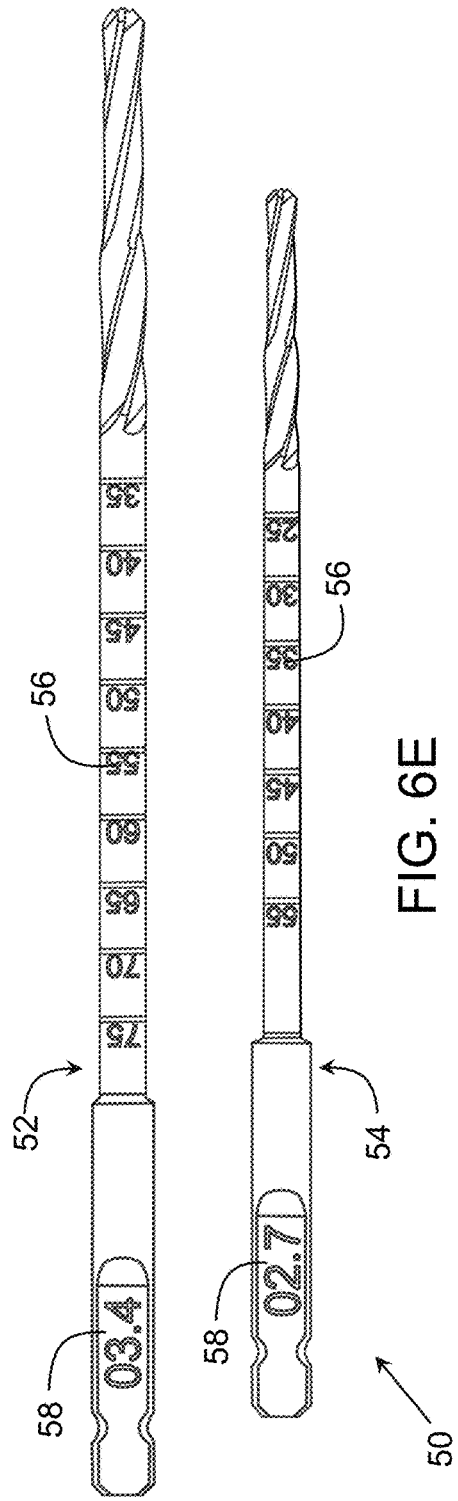

FIG. 6E illustrates a plurality of drill bits 50, with two differently sized drill bits 52, 54. The desired diameter and/or desired length obtained from the orthopedic tool can also be used to select an actual diameter of a drill bit 52, 54, as well as a depth of the bore formed by the drill bit. As shown, the drill bits 52, 54 can each include an actual diameter and depth markings 56, where the caregiver uses the desired diameter to select a drill bit and then can drill to an actual depth using the desired length as a guide.

The term "desired" when referring to desired length or desired diameter is intended to convey that the actual length/diameter of the selected implant does not necessarily need to be equal to the desired length/diameter. In some cases, the "desired" length and/or diameter will equal the actual length or diameter of the implant. In other cases, the actual length and/or diameter will be equal to the "desired" length and/or diameter.

Figure 6F:
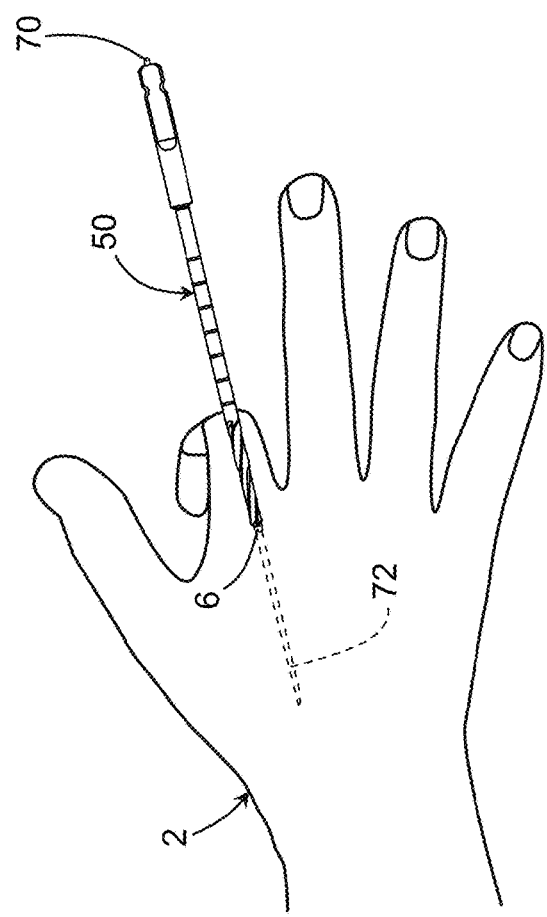

FIG. 6F illustrates use of a drill 50 over the orthopedic wire 70 to create a cavity or bore within the metacarpal bone in the hand 2 through the opening 6. The drill bit 50 can be used with any conventional hand or powered drill.

Figure 6G:
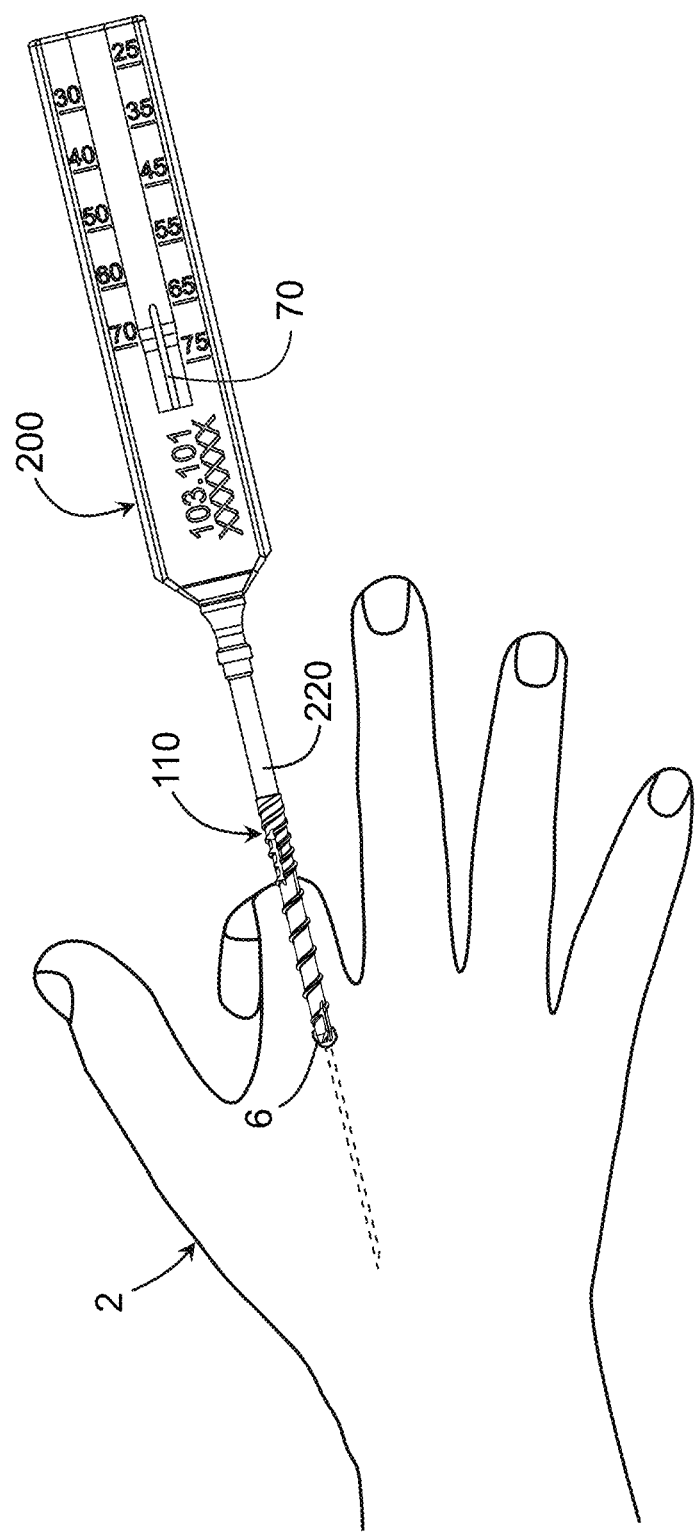

FIG. 6G illustrates use of the orthopedic tool 200 to drive an orthopedic implant 110 into the opening 6 in the hand 6. As shown, the drive surface (not visible in FIG. 6G) of the shaft 220 is inserted into the orthopedic implant 110 as described above. The orthopedic tool 200 drives the implant 110 into the anatomy over the orthopedic wire 70 via rotation of the orthopedic tool 200, which rotates the orthopedic implant 110. As discussed above, variations include driving the orthopedic implant 110 using a different driving mechanism. It is noted that in most procedures, the caregiver must reduce the fracture or dislocation of the anatomy due to muscles pulling on fractured/broken bones. In such a case, the caregiver will place the anatomy in a state of traction. Such a procedure is commonly known and omitted from the drawings for purposes of illustration of the improved features of the orthopedic tools within the invention.

Figure 7A:
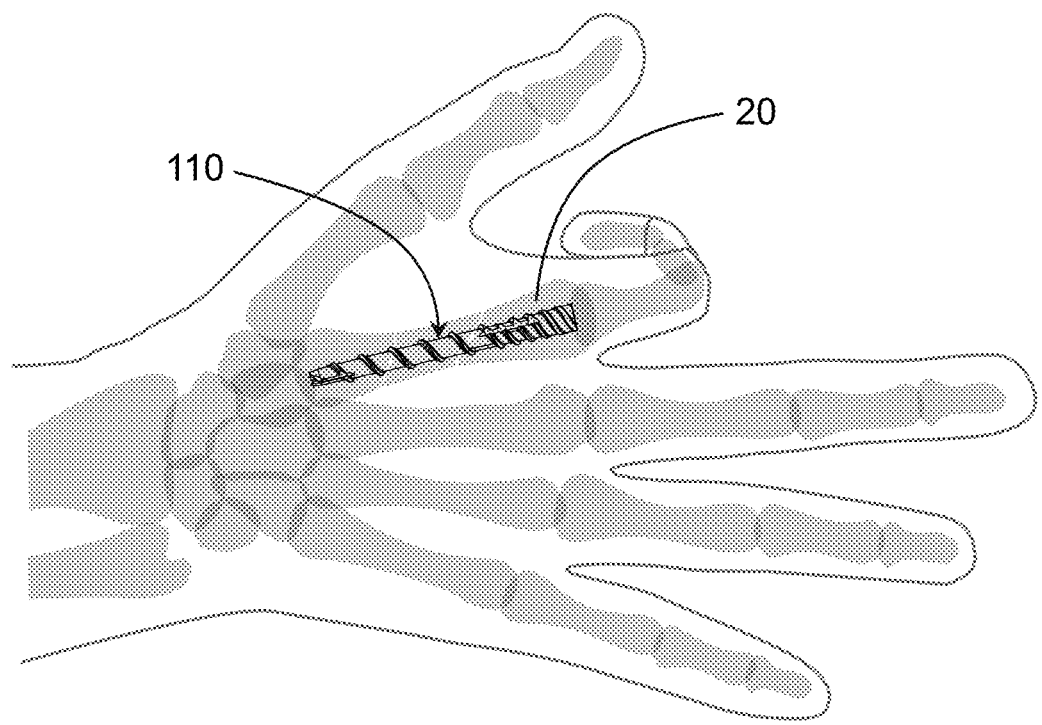
FIG. 7A illustrates a non-invasive image of an orthopedic implant positioned within a fractured metacarpal bone.
Figure 7B:
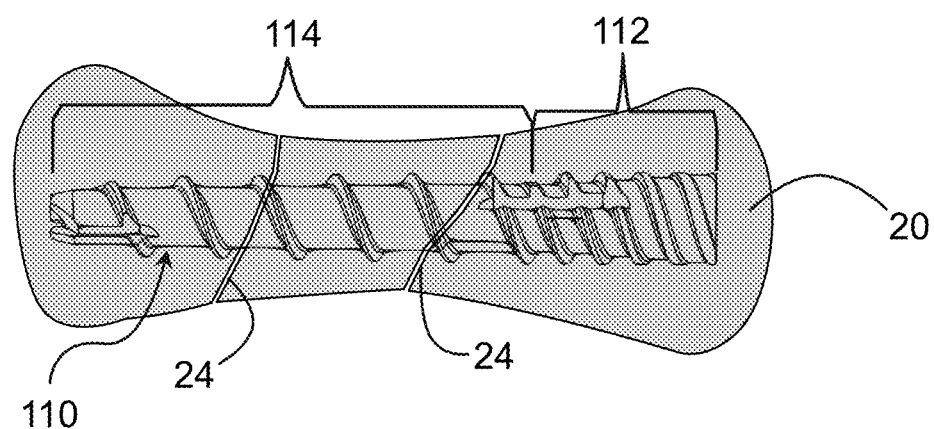
FIG. 7B illustrates an expanded view of the metacarpal bone of FIG. 7A.

FIG. 7A illustrates a non-invasive image of an orthopedic implant 110 positioned within a fractured metacarpal bone 20. FIG. 7B illustrates an expanded view of the metacarpal bone 20 of FIG. 7A, where the orthopedic implant 110 is implanted across fracture line 24 in the metacarpal bone 20. In this example, the orthopedic implant 110 is similar to that described above, where the orthopedic implant includes a distal segment 114 that functions as a nail (i.e., provides little compressive force when inserted) and a proximal segment 112 that comprises additional threaded structures to improve a purchase of the implant 110 within the metacarpal bone 20. As shown, this variation of the implant 110 includes a proximal segment 112 positioned within a head of the metacarpal bone 20, which increases in diameter over the medial portion of the bone.

Additional details of the methods, devices, systems, and kits regarding materials and manufacturing techniques may be employed within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a." "and." "said." and "the" include plural references unless the context clearly dictates otherwise.

It is important to note that where possible, aspects of the various described embodiments, or the embodiments themselves can be combined. Where such combinations are intended to be within the scope of this disclosure.

We claim:

1. A method for sizing an orthopedic implant intended for positioning in a cavity of an anatomic structure having an orthopedic wire extending from the cavity, the method comprising:

advancing an orthopedic tool over a proximal portion of the orthopedic wire where a distal portion of the orthopedic wire is in the cavity, the orthopedic tool having a handle with a plurality of length markers visible from an exterior of the orthopedic tool;

positioning a tip of the orthopedic tool adjacent to the anatomic structure where the proximal portion of the orthopedic wire remains within the orthopedic tool;

determining a desired length of the orthopedic implant by identifying a length marker from the plurality of length markers that is adjacent to a proximal end of the orthopedic wire; and selecting a length of the orthopedic implant using the desired length.

2. The method of claim 1, wherein the orthopedic tool includes a shaft extending from the handle, with a tool passage extending through both the handle and the shaft, where positioning the tip of the orthopedic tool adjacent to the anatomic structure comprises positioning a distal end of the shaft at least adjacent to the anatomic structure and positioning the proximal portion of the orthopedic wire within the orthopedic tool.

3. The method of claim 1, further comprising selecting a length of an orthopedic drill bit from a plurality of orthopedic drill bits using the desired length.

4. A method for sizing an orthopedic implant for positioning in a cavity of an anatomic structure, the method comprising:
   positioning an orthopedic tool over an exterior of the anatomic structure, where the orthopedic tool includes a driving shaft and a first implant sizing surface and a second implant sizing surface;
   aligning the first implant sizing surface along an axial centerline of the anatomic structure;
   obtaining a non-invasive image of the first implant sizing surface and the anatomic structure; and
   comparing a diametric dimension of the cavity to the first implant sizing surface and the second implant sizing surface on the non-invasive image to select a desired diameter corresponding to one of the first implant sizing surface or the second implant sizing surface;
   selecting a diameter of the orthopedic implant corresponding to the desired diameter.

5. The method of claim 4, further comprising selecting a diameter of an orthopedic drill bit from a plurality of orthopedic drill bits using the desired diameter.

6. A method for sizing an orthopedic implant for positioning in a cavity of an anatomic structure having an orthopedic wire extending from the cavity, the method comprising:
   positioning an orthopedic tool over an exterior of the anatomic structure, where the orthopedic tool includes a driving shaft extending from a handle, a first implant sizing surface on the driving shaft and a plurality of length markers visible from an exterior of the handle;
   aligning the first implant sizing surface along an axial centerline of the anatomic structure;
   obtaining a non-invasive image of the first implant sizing surface and the anatomic structure;
   selecting a diameter of the orthopedic implant using the non-invasive image to compare an outer dimension of the first implant sizing structure to a diametric dimension of the cavity;
   feeding a proximal portion of the orthopedic wire within orthopedic tool;
   positioning a tip of the driving shaft adjacent to the anatomic structure where the proximal portion of the orthopedic wire remains within the orthopedic tool and a distal portion of the orthopedic wire remains within the cavity;
   determining a desired length of the orthopedic implant by identifying a length marker from the plurality of length markers that is adjacent to a proximal end of the orthopedic wire;
   selecting a length of the orthopedic implant using the desired length;
   removing the orthopedic tool from the orthopedic wire;
   advancing the orthopedic implant having the diameter and the length into over the wire; and
   driving the orthopedic implant into the cavity using the orthopedic tool.

* * * * *